United States Patent [19]

Spatz

[11] Patent Number: 4,487,777
[45] Date of Patent: Dec. 11, 1984

[54] N-PHENYL-2-THIOMETHYLSUCCINIMIDES, AND N-PHENYL-2-THIOMETHENYL SUCCINIMIDES, AND FUNGICIDAL USE THEREOF

[75] Inventor: David M. Spatz, Fairfax, Calif.

[73] Assignee: Chevron Research Company, San Francisco, Calif.

[21] Appl. No.: 297,800

[22] Filed: Sep. 29, 1981

[51] Int. Cl.³ .................... A01N 37/32; A61K 31/40; C07D 207/40
[52] U.S. Cl. .................................... 424/274; 548/545
[58] Field of Search ................ 260/326.5 S, 326.55 F; 548/545; 424/274

[56] References Cited

U.S. PATENT DOCUMENTS 3,745,170  7/1923  Fujinami et al. .
3,903,090  9/1975  Fujinami et al. .
4,009,278  2/1927  Fujinami et al. .

FOREIGN PATENT DOCUMENTS 843836  11/1980  Belgium .................... 260/326.55 F Primary Examiner—Glennon H. Hollrah
Assistant Examiner—D. B. Springer
Attorney, Agent, or Firm—S. R. LaPaglia; T. G. DeJonghe; L. S. Squires

[57] ABSTRACT

N-phenyl-2-substituted succinimides represented by the formula

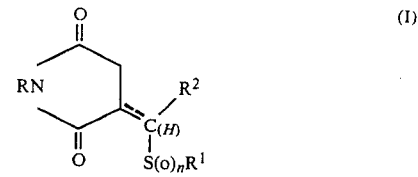

wherein R is phenyl or phenyl substituted with 1 to 3 of the same or different substituents selected from fluoro, chloro, bromo, iodo, nitro, and trihalo substituted methyl; $R^1$ is lower alkyl; lower alkyl substituted with 1 to 3 of the same or different halogens; lower alkenyl; lower alkenyl substituted with lower alkoxy or with 1 to 3 of the same or different halogens; lower alkynyl; lower alkynyl substituted with 1 to 3 of the same or different halogens; lower alkoxycarbonylalkylene; lower alkoxycarbonylalkylene substituted with 1 to 3 of the same or different halogens; lower acyl; a lower acyl substituted with 1 to 3 of the same of different halogens; a phenyl; a substituted phenyl with 1 to 3 of the same or different substituents selected from fluoro, bromo, chloro, nitro, lower alkyl, lower alkoxy, lower alkyl substituted with 1 to 3 of the same or different halogens;

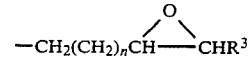

wherein n is 0, 1, 2 or 3 and $R^3$ is H or lower alkyl; $R^2$ is hydrogen or together with $R^1$ forms a heterocyclic ring system containing one or more sulfurs and no more than 4 carbon atoms, n is 0, 1 or 2 and the bond represented by C═C can be either saturated or unsaturated, when saturated, the carbon-carbon bond has 2 additional hydrogen atoms than the unsaturated bond, have good fungicidal activity.

12 Claims, No Drawings

N-PHENYL-2-THIOMETHYLSUCCINIMIDES, AND N-PHENYL-2-THIOMETHENYL SUCCINIMIDES, AND FUNGICIDAL USE THEREOF

BACKGROUND OF THE INVENTION

This invention is drawn to novel fungicides. In particular, I have found that N-phenyl-2-thiomethylsuccinimides and N-phenyl-2-thiomethenylsuccinimides possess good fungicidal activity.

Fujinami et al, U.S. Pat. Nos. 4,009,278, 3,903,090, and 3,745,170, disclose the synthesis and fungicidal activity of N-3,5-dichlorophenyl-2-alkylthiosuccinimides, N-3,5-dichlorophenyl-2-alkenylthiosuccinimides, N-3,5-dichlorophenyl-2-alkylsulfinylsuccinimides and N-3,5-dichlorophenyl-2-alkenylsulfinylsuccinimides.

SUMMARY OF THE INVENTION

The N-phenyl-2-substituted thiomethylsuccinimides of the invention are represented by the formula

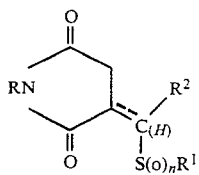

wherein R is phenyl or phenyl substituted with 1 to 3 of the same or different substituents selected from fluoro, chloro, bromo, iodo, nitro, and trihalo substituted methyl; $R^1$ is lower alkyl; lower alkyl substituted with 1 to 3 of the same or different halogens; lower alkenyl; lower alkenyl substituted with lower alkoxy or with 1 to 3 of the same or different halogens; lower alkoxycarbonylalkylene; lower alkoxycarbonylalkylkene substituted with 1 to 3 of the same or different halogens; lower acyl; a lower acyl substituted with 1 to 3 of the same or different halogens; a phenyl; a substituted phenyl with 1 to 3 of the same or different substituents selected from fluoro, chloro, bromo, iodo, nitro, lower alkyl, lower alkoxy, lower alkyl substituted with 1 to 3 of the same or different halogens;

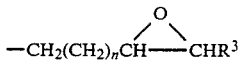

wherein n is 0, 1, 2 or 3 and $R^3$ is H or lower alkyl; $R^2$ is hydrogen or together with $R^1$ forms a heterocyclic ring system containing one or more sulfurs and no more than 4 carbon atoms; n is 0, 1 or 2 and the bond represented by C C can be either saturated or unsaturated, when saturated, the carbon-carbon bond has 2 additional hydrogen atoms than the unsaturated bond.

Among other factors, the present invention is based on my finding that the N-phenyl-2-thiomethylsuccinimides and the N-phenyl-2-thiomethenylsuccinimides of this invention are particularly effective as fungicides.

Preferred R groups are the 3,5 disubstituted phenyls. Preferably the 3,5 substituents are the same or different halogens, although other substituents are within the scope of the invention. Compounds of this invention show the greatest fungicidal activity when the R group is 3,5-dichlorophenyl.

The preferred $R^1$ substituents are the lower alkoxycarbonylalkylenes and the lower alkyls. Preferred lower alkoxycarbonylalkylene are ethoxycarbonylmethylene, methoxycarbonylmethylene, ethoxycarbonylethylene and methoxycarbonylethylene. Preferred lower alkyls are t-butyl and ethyl.

The preferred $R^2$ substituent is hydrogen although good fungicidal activity is found when $R^2$ together with $R^1$ forms a heterocyclic dithioketal ring system.

In part due to their superior fungicidal activity, the preferred class of compounds represented by formula I are those where the sulfur has been oxidized to the sulfone. The carbon-carbon bond shown in formula I may either be saturated or unsaturated. In the preferred embodiment the carbon-carbon bond is saturated.

Representative compounds of the invention include:
N-3,5-dichlorophenyl-2-allylthiomethylsuccinimide
N-3,5-dichlorophenyl-2-ethoxycarbonylmethylthiomethylsuccinimide
N-3,5-dichlorophenyl-2-ethoxycarbonylmethylsulfonylmethylsuccinimide
N-3,5-dichlorophenyl-2-methoxycarbonylmethylthiomethylsuccinimide
N-3,5-dichlorophenyl-2-methoxycarbonylmethylsulfonylmethylsuccinimide
N-3,5-dichlorophenyl-2-methoxycarbonylmethylsulfinylmethylsuccinimide
N-3,5-dichlorophenyl-2-ethoxycarbonylmethylsulfinylmethylsuccinimide
N-3,5-dichlorophenyl-2-t-butylthiomethenylsuccinimide
N-3,5-dichlorophenyl-2-t-butylsulfinylmethenylsuccinimide
N-3,5-dichlorophenyl-2-t-butylsulfonylmethenylsuccinimide
N-3,5-dichlorophenyl-2-phenylthiomethenylsuccinimide
N-3,5-dichlorophenyl-2-phenylsulfonylmethenylsuccinimide
N-3,5-dichlorophenyl-2-ethylthiomethenylsuccinimide
N-3,5-dichlorophenyl-2-ethylsulfinylmethenylsuccinimide
N-3,5-dichlorophenyl-2-ethylsulfonylmethenylsuccinimide
N-3,5-dichlorophenyl-2-thioacetylmethenylsuccinimide
N-3,5-dichlorophenyl-2-formylsuccinimide-2-dithioketal
N-3,5-difluorophenyl-2-ethoxycarbonylmethylthiomethylsuccinimide
N-3,5-difluorophenyl-2-ethoxycarbonylmethylsulfinylmethylsuccinimide
N-3,5-difluorophenyl-2-ethoxycarbonylmethylsulfonylmethylsuccinimide
N-3,5-dibromophenyl-2-ethoxycarbonylmethylthiomethylsuccinimide
N-3,5-dibromophenyl-2-ethoxycarbonylmethylsulfinylmethylsuccinimide
N-3,5-dibromophenyl-2-ethoxycarbonylmethylsulfonylmethylsuccinimide
N-3,5-[di-(trifluoromethyl)]phenyl-2-ethoxycarbonylmethylthiosuccinimide
N-3,5-dichlorophenyl-2-allylsulfonylmethylsuccinimide Definitions As used herein the following terms have the following meanings, unless expressly stated to the contrary.

The term "alkyl" refers to both straight- and branched-chain alkyl groups. The term "lower alkyl" refers both to straight- and branched-chain alkyl groups having a total of from 1 through 6 carbon atoms and includes primary, secondary, and tertiary alkyl groups. Typical lower alkyls include, for example, methyl, ethyl, n-propyl, isopropyl, n-butyl, t-butyl, n-hexyl and the like.

The term "alkynyl" refers to unsaturated alkyl groups having a triple bond (e.g. $CH_3C{\equiv}C(CH_2)_2{-}$) and includes both straight- and branched-chain alkynyl groups.

The term "lower alkynyl" refers to alkynyl groups having from 2 through 6 carbon atoms and includes, for example, but-3-ynyl; hex-4-ynyl; 3-methylpent-4-ynyl and the like.

The term "alkylene" refers to both straight- and branched-chain alkylene groups. The term lower alkylene refers to alkylene groups having from 1 through 6 carbon atoms. Typical alkylene groups include, for example, methylene, ethylene (i.e. $-CH_2CH_2-$), 2-methylpropylene

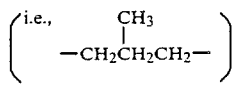

and the like.

The term "alkoxy" refers to the group $R^4O-$ wherein $R^4$ is alkyl. The term "lower alkoxy" refers to alkoxy groups having from 1 through 6 carbon atoms and includes, for example, methoxy, ethoxy, t-butoxy, hexoxy and the like.

The term "carbonyl" refers to the $>C{=}O$ group.

The term "alkoxycarbonyl alkylene" refers to the group

where $R^5$ is the alkylene portion of the group and $OR^4$ the alkoxy group, with both terms having the meaning defined above.

The term "lower alkoxycarbonyl alkylene" refers to the group

where $R^5$ is of 1 through 6 carbon atoms, and $R^4$ is also of 1 through 6 carbon atoms. Typical examples of alkoxycarbonyl alkylene groups are ethoxycarbonyl methylene

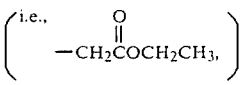

ethoxycarbonyl ethylene

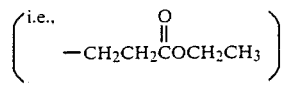

The term "halogen or halo atom" refers to the group fluoro, chloro, iodo, and bromo.

The term "acyl" refers to the group

where $R^6$ is alkyl. The term "lower acyl" refers to the acyl group having 1 through 6 carbon atoms.

The term "alkenyl" refers to unsaturated alkyl groups having a double bond (e.g., $CH_3CH{=}CH(CH_2)_2{-}$,) and includes both straight- and branched-chain alkenyl groups.

The term "lower alkenyl" groups refers to alkenyl groups having from 2 through 6 carbon atoms. Typical lower alkenyl groups include, for example, ethylene; but-3-enyl; hex-4-enyl; 2-methylpent-4-enyl and the like.

The term "alkoxy" refers to the group $R^4O-$ wherein $R^4$ is alkyl. The term "lower alkoxy" refers to alkoxy groups having from 1 through 6 carbon atoms and includes, for example, methoxy, ethoxy, t-butoxy hexoxy, and the like.

DETAILED DESCRIPTION OF THE INVENTION

Compounds of formula I are prepared by the following methods. When the 2-substituent on the N-succinimide is saturated, the products are prepared by initially reacting a substituted aniline with an essentially equimolar amount of 2-methenylsuccinic anhydride (itaconic anhydride) using a catalytic amount of an acid (H+) as shown in reaction 1:

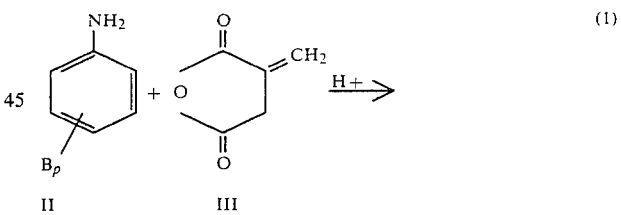

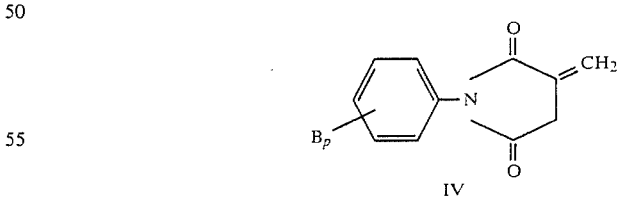

where $B_p$ represents possible substituents on the phenyl ring. The reaction is conducted in the liquid phase using an inert organic liquid such as xylene, toluene, benzene, tetrahydrofuran and the like. Xylene is the preferred solvent in reaction 1. The acid (H+) used as the catalyst may be organic or inorganic. The preferred acid is inorganic such as hydrochloric, sulfuric, nitric and the like. Most preferably, the inorganic acid used is sulfuric. Reaction pressure is not critical. For convenience, the reaction pressure is generally atmospheric. A Dean- Stark trap is used to remove water generated in the reaction system. The reaction is heated at reflux until the amount of water collected in the Dean-Stark trap indicates that the reaction is complete. This is usually accomplished within 1 to 18 hours. The N-phenyl-2-methenylsuccinimide, compound IV, is isolated by conventional procedures such as extraction, filtration, chromatography, distillation, or alternatively, is used directly in reaction (2) without purification and/or isolation.

Intermediate IV is next reacted with an essentially equimolar amount of $HSR^1$, compound V, using a catalytic amount of a base (B) to give product VI as shown in reaction 2 below:

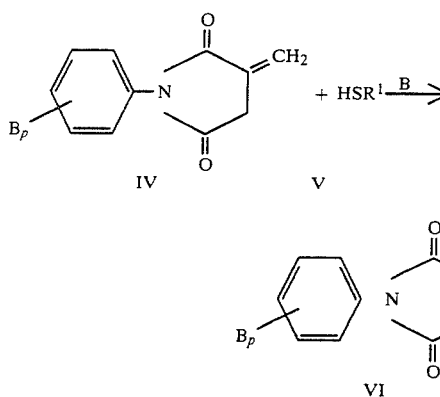

(2)

where $R^1$ is as defined above. The reaction is conducted in the liquid phase using an inert organic liquid such as dimethoxyethane, tetrahydrofuran, dichloromethane, chloroform and the like. The preferred solvent is dimethoxyethane. The base used may be organic or inorganic. The preferred base is an organic base such as triethylamine, pyridine and the like. Most preferably a catalytic amount of triethylamine (approximately 0.1 ml) is used. Reaction pressure is not critical. For convenience, the the reaction pressure is generally atmospheric. The reaction is conducted at a temperature of 0° C. to 100° C. and is generally complete within 1 to 24 hours. The product is isolated by conventional procedures such as extraction, filtration, chromatography, distillation, or alternatively is used directly in reactions 3 or 4 without purification and/or isolation.

Product VI is converted to the sulfoxide by reaction with one equivalent of m-chloroperbenzoic acid (VII) as shown in reaction 3.

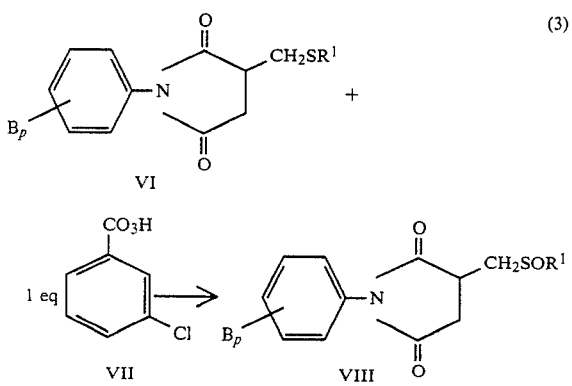

(3)

The reaction is conducted in the liquid phase using an inert organic liquid such as dichloromethane, chloroform, acetone and the like. In these systems, dichloromethane is the preferred solvent. Reaction pressure is not critical. For convenience, the reaction pressure is generally atmospheric. The reaction is conducted at a temperature of 0° C. to 100° C. and is generally complete within 1 to 72 hours. After completion, the system is treated with an aqueous base solution so as to remove any remaining m-chloroperbenzoic acid. The resulting sulfoxide, VIII, is isolated by conventional procedures such as extraction, filtration, chromatography, distillation and the like.

Product VI may also be converted to the sulfone by reaction with 2 equivalents of m-chloroperbenzoic acid (VII) as shown in reaction 4.

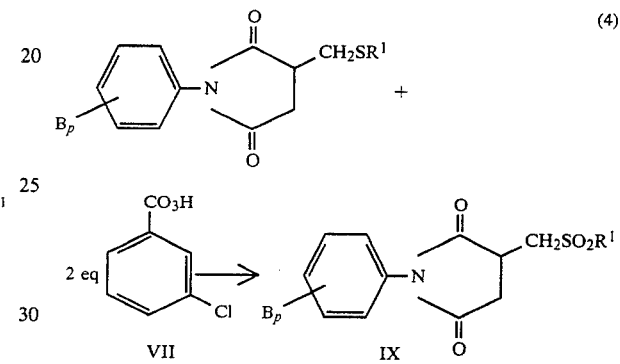

(4)

The reaction conditions are identical to those in Reaction 3. Alternatively, the sulfone may be prepared by oxidation of the sulfide with potassium hydrogen persulfate (oxone) in a methanol-water solvent. The resulting sulfone, IX, is isolated by conventional procedures such as extraction, filtration, chromatography, distillation and the like.

When the 2-substituent on the succinimide is unsaturated, the products are prepared by initially reacting N-phenylsuccinimide with an essentially equimolar amount of a dimethylformamide acetal as shown in reaction 5:

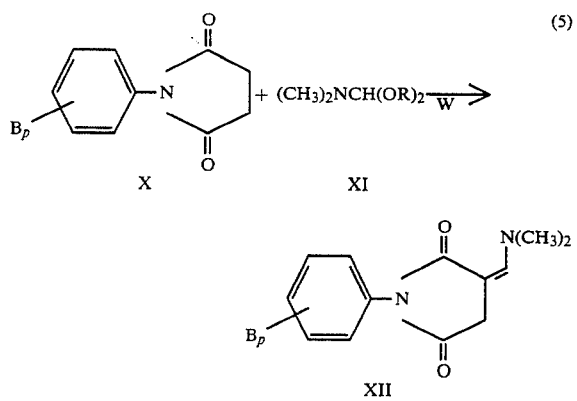

(5)

where R is alkyl and Bp is as defined above. The reaction is conducted in the liquid phase using an excess of the dimethylformamide acetal or in an inert organic liquid such as xylene, toluene, benzene, tetrahydrofuran and the like. Xylene is the preferred solvent for reaction 5. Reaction pressure is not critical. For convenience, reaction pressure is generally atmospheric. The reaction is heated at reflux and is generally complete within 1 to 24 hours. Use of any dimethylformamide acetal is possible in reaction 5 but greatest yields of XII are obtained when dimethylformamide dineopentyl acetal is used. The resulting N-phenyl-2-dimethylaminomethenylsuccinimide, XII, is isolated as a mixture of E and Z isomers by conventional procedures such as extraction, filtration, chromatography, distillation or alternatively is used directly in reaction 6 without purification and/or isolation.

The N-phenyl-2-dimethylaminomethenylsuccinimide, XII, is converted to the unsaturated sulfides, of formula I by reacting essentially equimolar amounts of XII with R$^1$SH (V) using a stoichiometric amount of an acid, H+, as shown in reaction 6:

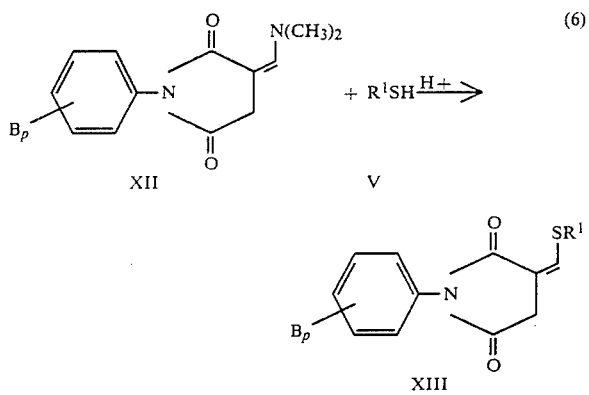

where R$^1$ is as defined above. The reaction is conducted in the liquid medium using an inert organic liquid such as xylene, toluene, benzene and the like. The preferred acid is an organic acid such as p-toluenesulfonic acid and the like. Reaction pressure is not critical. For convenience, reaction pressure is generally atmospheric. The reaction is conducted at a temperature of 0° C. to 120° C. and is generally complete within 1 to 24 hours. The resulting sulfide, XIII, is isolated as a mixture of E and Z isomers by conventional procedures such as extraction, filtration, chromatography and distillation.

The vinyl sulfides, XIII, are converted to the corresponding sulfoxides and sulfones by the procedures described for reactions 3 and 4.

Utility

The compounds of this invention are useful for controlling fungi, particularly plant fungal infections caused by *Botrytis cinerea*, leaf blights caused by such organisms as *Phytophthora infestans conidia, Alternaria solani conidia, Septoria apii,* downy mildew caused by organisms such as *Plasmopara viticola* and other fungal infections caused by organisms such as *Rhizoctania solani.*

However, some fungicidal compounds of the invention may be more fungicidally active then others against particular fungi. Tables III and VI list a summary of activity against some particular fungi for several compounds of this invention.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried no relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLE 1

Preparation of N-3,5-dichlorophenyl-2-methenylsuccinimide

2-Methenylsuccinic anhydride (itaconic anhydride), 22.4 g, was added to 400 ml of xylene. 32.4 g of 3,5-dichloroaniline was then added to the system followed by addition of 0.2 ml sulfuric acid. The system was heated at reflux for 6 hours until the theoretical amount of water was removed via a Dean-Stark trap. The xylene was removed by stripping to give the crude N-3,5-dichlorophenyl-2-methenyl-succinimide. The product was recrystallized from ethanol to give 30 g. of a white crystal. m.p. 136°–138°.

Examination by NMR and IR spectroscopy was in complete accord with the proposed structure.

EXAMPLE 2

Preparation of N-3,5-dichlorophenyl-2-ethoxycarbonylmethylthiomethylsuccinimide

N-3,5-dichlorophenyl-2-methenylsuccinimide, 7.5 g, were added to 50 ml of dimethoxyethane. 3.6 g of ethylmercaptoacetate, along with 0.1 ml of triethylamine, were added to the system. The reaction was stirred at room temperature for 20 hours. The dimethoxyethane was removed by stripping to give 9.7 g of the N-3,5-dichlorophenyl-2-ethoxycarbonylmethylthiomethylsuccinimide.

Examination by NMR and IR spectroscopy was in complete accord with the proposed structure. Elemental analysis plus other physical data for this compound are found in Table I, compound number 4.

EXAMPLE 3

Preparation of N-3,5-dichlorophenyl-2-ethoxycarbonylmethylsulfinylmethylsuccinimide N-3,5-dichlorophenyl-2-ethoxycarbonylmethylthiomethylsuccinimide, 7.0 g, is added to 50 ml of dichloromethane. 4.0 g of m-chloroperbenzoic acid is slowly added to the system. The system is stirred for 20 hours. The system is washed with 2×50 mls sodium bicarbonate, then washed with water and filter. The dichloromethane is dried with magnesium sulfate and the dichloromethane is then removed by stripping to give the N-3,5-dichlorophenyl-2-ethoxycarbonylmethylsulfinylmethylsuccinimide.

EXAMPLE 4

Preparation of N-3,5-dichlorophenyl-2-ethoxycarbonylmethylsulfonylmethylsuccinimide N-3,5-dichlorophenyl-2-ethoxycarbonylmethylthiomethylsuccinimide, 7.0 g, was added to 50 ml of dichloromethane. 8.0 g of m-chloroperbenzoic acid were slowly added to the system. The system was stirred for 20 hours. Afterwards, the system was washed with 2×50 mls sodium bicarbonate, the system was then washed with water and filtered. The dichloromethane was dried with magnesium sulfate and the dichloromethane removed by stripping to give 5.4 g of the N-3,5-dichlorophenyl-2-ethoxycarbonylmethylsulfonylmethylsuccinimide. m.p. 106°–108° C.

Examination by NMR and IR spectroscopy was in complete accord with the proposed structure. Elemental analysis plus other physical data for this compound are found in Table I, compound number 3.

EXAMPLE 5

Preparation of N-3,5-dichlorophenyl-2-thioacetylmethylsuccinimide

N-3,5-dichlorophenyl-2-methenylsuccinimide, 7.6 g, was added to 100 ml of dimethoxyethane. 2.3 g of thiolacetic acid along with 0.1 ml of triethylamine were added to the system. The reaction was stirred at room temperature for 20 hours. The dimethoxyethane was removed by stripping to give 9.5 g of the N-3,5-dichlorophenyl-2-thioacetylmethylsuccinimide.

Examination by NMR and IR spectroscopy was in complete accord with the proposed structure. Elemental analysis plus other physical data for this compound are found in Table I compound 5.

EXAMPLE 6

Preparation of N-3,5-dichlorophenyl-2-dimethylaminomethenylsuccinimide

N-3,5-dichlorophenylsuccinimide, 4.88 g, was added to 100 ml of xylene. 4.64 g (5.6 mls) of N,N-dimethylformamide dineopentyl acetal was added to the system. The system was heated at reflux for 1½ hours. Upon cooling a yellowish-white precipitate fell out. The system was then cooled in an ice bath. The precipitate was filtered and dried to give 1.5 g of the N-3,5-dichlorophenyl-2-dimethylaminomethenylsuccinimide. m.p. 220°–224° C.

Examination by NMR and IR spectroscopy was in complete accord with the proposed structure.

|   | Theory | Found |
|---|--------|-------|
| C | 52.18  | 54.28 |
| H | 4.04   | 4.58  |
| N | 9.36   | 9.64  |

EXAMPLE 7

Preparation of the N-3,5-dichlorophenyl-2-t-butylthiomethenylsuccinimide

N-3,5-dichlorophenyl-2-dimethylaminomethenylsuccinimide, 3.0 g, was added to 30 ml of toluene. 0.9 g of t-butyl mercaptan (1.12 ml) along with 1.9 g of p-toluenesulfonic acid were added to the system. The system was heated at reflux for 3 hours. The toluene was removed by stripping and the residue dissolved in 50 ml of dichloromethane. The dichloromethane solution was washed with water and then dried with magnesium sulfate. The dichloromethane was removed by stripping to 1.6 g of a mixture of the E and Z isomers of the N-3,5-dichlorophenyl-2-t-butylthiomethenylsuccinimide. m.p. 120°–122° C.

Examination by NMR and IR spectroscopy was in complete accord with the proposed structure.

EXAMPLE 8

Preparation of the N-3,5-dichlorophenyl-2-formylsuccinimide-2-dithioketal

N-3,5-dichlorophenyl-2-dimethylaminomethenylsuccinimide, 4.5 g, was added to 50 ml of toluene. 1.47 g (1.31 ml) of 1,2 ethanedithiol along with 2.8 g p-toluenesulfonic acid were added to the system. The system was heated at reflux for 6 hours. The toluene was removed by stripping and the residue dissolved in dichloromethane. The dichloromethane solution was washed with water and then dried over magnesium sulfate. The dichloromethane was removed by stripping to give several products. The mixture was separated on HPLC using 2.5% ethyl acetate in dichloromethane to give 2.8 g of the N-3,5-dichlorophenyl-2-formylsuccinimide-2-dithioketal m.p. 115°–117° C.

Examination by NMR and IR spectroscopy was in complete accord with the proposed structure.

Other compounds prepared in accordance with Examples 1 through 8 are found in Table I and Table II.

EXAMPLE 9

Preparation of N-3,5-dichlorophenyl-2-thiotrichlorocetylmethylsuccinimide

N-3,5-dichlorophenyl-2-methenylsuccinimide, 7.0 gm is added to 100 ml of dimethoxyethane. 5.0 gm of trichlorothiolacetic acid, which is prepared in accordance with U.S. Pat. No. 3,428,665 and incorporated herein by reference, along with 0.1 ml of triethylamine is added to the system. The reaction is stirred at room temperature for 20 hours. The dimethoxyethane is removed by stripping to give the N-3,5-dichlorophenyl-2-trichloroacetylthiomethylsuccinimide.

EXAMPLE 10

Preparation of N-3,5-dichlorophenyl-2-trichloromethylthiomethenylsuccinimide

N-3,5-dichlorophenyl-2-dimethylaminomethenylsuccinimide, 2.0 gm, is added to 30 ml of toluene. 1.1 gm of trichloromethyl mercaptan, which is prepared in accordance with chemical abstracts 70:151458W and incorporated herein by reference, along with 0.1 ml of trimethylamine is added to the system. The reaction is stirred at room temperature for 20 hours. The dimethoxyethane is removed by stripping to give the N-3,5-dichlorophenyl-2-trichloromethylthiomethenylsuccinimide.

Other compounds which are prepared in accordance with Examples 9 and 10 include:
N-3,5-dichlorophenyl-2-(2,4-dichlorophenyl)thiomethylsuccinimide;
N-3,5-dichlorophenyl-2-(3,5-dibromophenyl)thiomethylsuccinimide;
N-3,5-dichlorophenyl-2($\beta,\beta,\beta$-trichloroethoxy)carbonylmethylsulfonylmethylsuccinimide;
N-3,5-dichlorophenyl-2-($\beta,\beta,\beta$-trichloroethoxy)carbonylmethylsulfonylmethyenylsuccinimide.

EXAMPLE 11

Grape Downy Mildew Control

The compounds of the invention were tested for the control of the grape downy mildew organism *Plasmapora viticola*. Detached leaves, between 70 and 85 mm in diameter, of 7-week-old *Vitis vinifera* cultivar Emperor grape seedlings were used as hosts. The leaves were sprayed with a solution of the test compound in acetone. The sprayed leaves were dried, inoculated with a spore suspension of the organism, placed in a humid environmental chamber and incubated at 66°–68° F. and about 100% relative humidity. After incubation for 2 days, the plants were then held in a greenhouse for seven to nine days. Afterwards, the amount of disease control was determined. The percent disease control provided by a given test compound was based on the percent disease reduction relative to untreated check plants. The results are tabulated in Table III.

EXAMPLE 12

Tomato Late Blight

Compounds of the invention were tested for the control of the Tomato Late Blight organism Phytophthora infestans conidia. Five- to six-week-old tomato (variety Bonny Best) seedlings were used. The tomato plants were sprayed with a 250-ppm solution of the test compound in acetone, water and a small amount of a non-ionic emulsifier. The sprayed plants were then inoculated one day later with the organism, placed in an environmental chamber and incubated at 66°–68° F. and 100% relative humidity for at least 16 hours. Following the incubation, the plants were allowed to dry and then were maintained in a greenhouse for approximately 7 days. The percent disease control provided by a given test compound was based on the percent disease reduction relative to untreated check plants. The compounds giving effective control at the test concentration are tabulated in Table II.

EXAMPLE 13

Tomato Early Blight

Compounds of the invention were tested for the control of the Tomato Early Blight organism, *Alternaria solani conidia*. Tomato (variety Bonny Best) seedlings of 6 to 7 weeks old were used. The tomato plants were sprayed with a 250-ppm solution of the test compound in an acetone-and-water solution containing a small amount of a non-ionic emulsifier. The sprayed plants were inoculated one day later with the organism, placed in the environmental chamber and incubated at 66°–68° F. and 100% relative humidity for 24 hours. Following the incubation, the plants were maintained in the greenhouse for about 12 days. Percent disease control was based on the percent disease development on untreated check plants. The compounds giving effective control at the test concentration are tabulated in Table V.

EXAMPLE 14

Celery Late Blight

Compounds of the invention were tested for the control of Celery Late Blight using celery (Utah) plants 11 weeks old. The Celery Late Blight organism was *Septoria apii*. The celery plants were sprayed with solutions of the candidate toxicant mixed with acetone, water and a non-ionic emulsifier. The plants were then inoculated with the organism and placed in an environmental chamber and incubated at 66°–68° F. in 100% relative humidity for an extended period of time (approximately 48 hours). Following the incubation, the plants were allowed to dry and then were maintained in a greenhouse humidity for approximately 14 days. The percent disease control provided by a given candidate toxicant is based on the percent disease reduction relative to untreated check plants. The compounds giving effective control at the test concentrations are reported in Table V.

EXAMPLE 15-*Botrytis Cinerea* Control

Compound 1 of the invention was tested as a preventive fungicide against *Botrytis cinerea* on harvested mature grape berries (variety Emperor) by the following procedure: four grape bunches (trimmed to approximately 30 berries) were sprayed with a solution of the test compound in a solution of water, acetone and a small amount of a non-ionic emulsifier. The sprayed grapes were inoculated approximately one day later with 2- to 3-week-old culture of *Botrytis cinerea* grown on potato dextrose agar plates. The rate of disease incidence was determined 5–10 days after inoculation, when disease symptoms are fully evident on non-treated check grapes. Infection is determined by actual count of the number of infected berries. The percent disease control provided by a test compound was calculated from the percentage disease reduction based on the non-treated check grapes. The concentration of the test compound and the results are tabulated in Table IV.

EXAMPLE 16

Rhizoctonia

Compounds of the present invention were evaluated for effectiveness against *Rhizoctonia solani* by means of a mycelial inhibition test. This test is designed to measure the fungitoxic activity of fungicidal chemicals in terms of their degree of inhibition of mycelial growth. Each compound to be tested was dissolved in acetone to 500 ppm concentration. Paper strips were infused with the particular mycelium growth (on this case *Rhizoctonia solani*) by covering the paper with a potato dextrose broth culture of mycelial suspension. The papers were then placed on potato dextrose agar plates and sprayed by means of a microsprayer with the fungicidal solution. The treated paper strips were incubated at 25° C. and data taken after 24 hours. Fungicidal activity is measured by the zone of inhibited mycelial growth from the center of the paper strip. The effectiveness of the compounds tested for fungicidal activity against *Rhizoctonia solani* is reported in Table III in terms of the $$\frac{\text{Micrograms/cm}^2 \text{ for 99\% control of the fungus (of test compound)}}{\text{Micrograms/cm}^2 \text{ for 99\% control of the fungus (of Standard)}} \times 100$$

In cases where greater than 1.6 micrograms/cm$^2$ were required for 99% control, a value of "0" was assigned to the test compound.

TABLE I

Compounds of the Formula

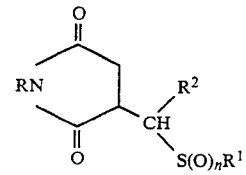

| Compound No. | R | R$^1$ | R$^2$ | n | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 1 | 3,5-Cl$_2$—φ | CH$_2$CO$_2$CH$_3$ | H | 2 | 42.66 | 42.81 | 3.30 | 3.60 | 3.55 | 3.28 | white solid | 80–83° C. |
| 2 | 3,5-Cl$_2$—φ | CH$_2$CH$_2$CO$_2$CH$_3$ | H | 2 | 44.14 | 44.86 | 3.67 | 3.99 | 3.43 | 3.52 | white solid | 158–160° C. |
| 3 | 3,5-Cl$_2$—φ | CH$_2$CO$_2$Et | H | 2 | 44.12 | 45.9 | 3.70 | 3.46 | 3.43 | 3.52 | white solid | 106–108° C. |
| 4 | 3,5-Cl$_2$—φ | CH$_2$CO$_2$Et | H | 0 | 47.96 | 45.53 | 3.73 | 3.74 | 3.59 | 3.64 | oil | |
| 5 | 3,5-Cl$_2$—φ | $\overset{\text{O}}{\underset{}{\overset{\|}{\text{C}}}}$CH$_3$ | H | 0 | 46.96 | 47.31 | 3.34 | 3.52 | 4.22 | 4.29 | yellow solid | 108–110° C. |
| 6 | 3,5-Cl$_2$—φ | CH$_2$CO$_2$CH$_3$ | H | 0 | 46.43 | 45.43 | 3.59 | 3.79 | 3.86 | 3.82 | oil | |
| 7 | 3,5-Cl$_2$—φ | CH$_2$CH$_2$CO$_2$CH$_3$ | H | 0 | 47.89 | 47.55 | 3.99 | 4.19 | 3.72 | 3.86 | oil | |
| 8 | 3,5-Cl$_2$—φ | —CH$_2$CH$_2$S— | | 0 | 44.83 | 47.22 | 3.18 | 3.79 | 4.02 | 4.15 | white solid | 115–117° C. |
| 9 | 3,5-Cl$_2$—φ | CH$_2$CH=CH$_2$ | H | 2 | 46.41 | 46.76 | 3.62 | 3.96 | 3.87 | 3.15 | yellow oil | |
| 10 | 3,5-Cl$_2$—φ | CH$_2$C=CH$_2$<br>\|<br>Cl | H | 2 | 42.38 | 45.79 | 3.05 | 4.12 | 3.53 | 3.36 | yellow oil | |

TABLE II

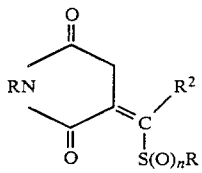

| Compound No. | R | R¹ | R² | n | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 11 | 3,5-Cl$_2$—φ | C(CH$_3$)$_3$ | H | 2 | 47.88 | 48.6 | 4.02 | 4.2 | 3.72 | 3.8 | white solid | 128–130° C. |
| 12 | 3,5-Cl$_2$—φ | φ | H | 0 | 56.05 | 57.76 | 3.04 | 3.35 | 3.85 | 3.84 | yellow solid | 132–135° C. |
| 13 | 3,5-Cl$_2$—φ | CH$_2$CH$_3$ | H | 0 | 49.31 | 50.35 | 3.50 | 3.94 | 4.43 | 4.39 | off-white solid | 148–151° C. |
| 14 | 3,5-Cl$_2$—φ | C(CH$_3$)$_3$ | H | 0 | 52.33 | 54.75 | 4.39 | 4.96 | 4.07 | 4.44 | white solid | 120–122° C. |

TABLE III

| Compound Number | % Control | | | | |
|---|---|---|---|---|---|
| | TLB | CLB | TEB | Grape DM | Rhizoc |
| 1 | 11 | 57 | 89 | 81 | 0 |
| 2 | 23 | 45 | 96 | 71 | 0 |
| 3 | 93 | — | 85 | 23 | 78 |
| 4 | 84 | — | 0 | 0 | 0 |
| 5 | 0 | 0 | 57 | 23 | 0 |
| 6 | 39 | 50 | 80 | 18 | 0 |
| 7 | 21 | 0 | 89 | 97 | 0 |
| 8 | 89 | 29 | 98 | 18 | 30 |
| 9 | 25 | 50 | 63 | 57 | 80 |
| 10 | 29 | 50 | 83 | 18 | 91 |
| 11 | 6 | 0 | 0 | 8 | 0 |
| 12 | 21 | 0 | 0 | 0 | 0 |
| 13 | 0 | 0 | 94 | 35 | 0 |
| 14 | 67 | 57 | 96 | 42 | 0 |

TLB — Tomato Late Blight
CLB — Celery Late Blight
TEB — Tomato Early Blight
Grape DM — Grape Downy Mildew
Rhizoc. — Rhizoctonia - standard used was Difolatan ®

TABLE IV

| Compound Number | Botrytis Prevention (% Control) | | |
|---|---|---|---|
| | 250 ppm | 100 ppm | 40 ppm |
| 1 | 58 | 52 | 58 |

What is claimed is:

1. A compound having the formula

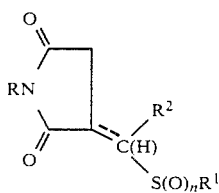

wherein R is phenyl or phenyl substituted with 1 to 3 of the same or different substituents selected from fluoro, chloro, bromo, iodo, nitro, and trihalo substituted methyl;

R¹ is lower alkoxycarbonylalkylene wherein said alkoxy moiety and said alkylene moiety independently have 1 through 6 carbon atoms;

R² is hydrogen or R¹ and R² together with the carbon atom to which they are joined form a sulfur heterocycle having the formula

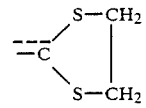

n is 0, 1, 2, or 3, with the proviso that when R¹ and R² together with the carbon atom to which they are joined form said sulfur heterocycle then n is 0; and C--C represents either a saturated single bond or an unsaturated double bond.

2. A compound of the formula defined in claim 1 wherein R¹ is lower alkoxycarbonylalkylene.

3. A compound of the formula defined in claim 2 wherein R¹ is ethoxycarbonylmethylene.

4. A compound of the formula defined in claim 1 wherein R is phenyl substituted with 1 to 3 of the same or different substituents selected from fluoro, chloro, bromo.

5. A compound of the formula defined in claim 4 wherein R is 3,5-dichlorophenyl.

6. A compound of the formula defined in claim 5 wherein R¹ is ethoxycarbonylmethylene, R² is hydrogen, n is 2 and the carbon-carbon bond is saturated.

7. A compound of the formula defined in claim 5 wherein R¹ is methoxycarbonylmethylene, R² is hydrogen, n is 2 and the carbon-carbon bond is saturated.

8. A compound of the formula defined in claim 5 wherein R¹ together with R² forms said sulfur heterocycle radical, n is zero and the carbon-carbon bond is saturated.

9. A method for preventing the fungal disease tomato late blight in tomato plants, which comprises applying to said plants a non-phytotoxic fungicidally effective amount of the compound of claim 1.

10. A method for preventing fungal diseases selected from the group of tomato late blight and tomato early blight; which comprises, respectively, applying to tomato plants a non-phytotoxic fungicidally effective amount of the compound of claim 6.

11. An agricultural fungicidal composition for controlling tomato late blight comprising a biologically inert carrier and a non-phytotoxic fungicidally effective amount of the compound of claim 1 effective to prevent tomato late blight in tomato plants.

12. The compound of claim 1 wherein said —C carbon-carbon bond is saturated.

* * * * *